(12) United States Patent
Stafford

(10) Patent No.: US 7,883,464 B2
(45) Date of Patent: Feb. 8, 2011

(54) INTEGRATED TRANSMITTER UNIT AND SENSOR INTRODUCER MECHANISM AND METHODS OF USE

(75) Inventor: Gary Ashley Stafford, Hayward, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 700 days.

(21) Appl. No.: 11/240,257

(22) Filed: Sep. 30, 2005

(65) Prior Publication Data

US 2007/0078320 A1    Apr. 5, 2007

(51) Int. Cl.
 *A61B 5/00*    (2006.01)
(52) U.S. Cl. .................. 600/309; 600/347; 600/365
(58) Field of Classification Search .............. 600/347, 600/365, 309
See application file for complete search history.

(56) References Cited

U.S. PATENT DOCUMENTS

| | | | |
|---|---|---|---|
| 3,123,790 A | 3/1964 | Tyler | |
| 3,581,062 A | 5/1971 | Aston | |
| 3,926,760 A | 12/1975 | Allen et al. | |
| 3,949,388 A | 4/1976 | Fuller | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,373,527 A | 2/1983 | Fischell | |
| 4,425,920 A | 1/1984 | Bourland et al. | |
| 4,478,976 A | 10/1984 | Goertz et al. | |
| 4,494,950 A | 1/1985 | Fischell | |
| 4,509,531 A | 4/1985 | Ward | |
| 4,527,240 A | 7/1985 | Kvitash | |
| 4,538,616 A | 9/1985 | Rogoff | |
| 4,619,793 A | 10/1986 | Lee | |
| 4,671,288 A | 6/1987 | Gough | |
| 4,685,466 A * | 8/1987 | Rau | 600/387 |
| 4,703,756 A | 11/1987 | Gough et al. | |
| 4,711,247 A * | 12/1987 | Fishman | 600/556 |
| 4,729,672 A | 3/1988 | Takagi | |
| 4,731,726 A | 3/1988 | Allen, III | |
| 4,749,985 A | 6/1988 | Corsberg | |
| 4,757,022 A | 7/1988 | Shults et al. | |
| 4,777,953 A | 10/1988 | Ash et al. | |

(Continued)

FOREIGN PATENT DOCUMENTS

DE    4401400    7/1995

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner*—Charles A Marmor, II
*Assistant Examiner*—Karen E Toth
(74) *Attorney, Agent, or Firm*—Jackson & Co., LLP

(57) ABSTRACT

Method and apparatus for providing an integrated transmitter unit and sensor insertion mechanism is provided.

25 Claims, 9 Drawing Sheets

U.S. PATENT DOCUMENTS

| | | | |
|---|---|---|---|
| 4,779,618 A | 10/1988 | Mund et al. | |
| 4,854,322 A | 8/1989 | Ash et al. | |
| 4,890,620 A | 1/1990 | Gough | |
| 4,895,147 A | 1/1990 | Bodicky et al. | |
| 4,925,268 A | 5/1990 | Iyer et al. | |
| 4,953,552 A | 9/1990 | DeMarzo | |
| 4,986,271 A | 1/1991 | Wilkins | |
| 4,988,341 A | 1/1991 | Columbus et al. | |
| 4,995,402 A | 2/1991 | Smith et al. | |
| 5,000,180 A | 3/1991 | Kuypers et al. | |
| 5,002,054 A | 3/1991 | Ash et al. | |
| 5,013,161 A | 5/1991 | Zaragoza et al. | |
| 5,019,974 A | 5/1991 | Beckers | |
| 5,050,612 A | 9/1991 | Matsumura | |
| 5,055,171 A | 10/1991 | Peck | |
| 5,082,550 A | 1/1992 | Rishpon et al. | |
| 5,106,365 A | 4/1992 | Hernandez | |
| 5,122,925 A | 6/1992 | Inpyn | |
| 5,140,985 A * | 8/1992 | Schroeder et al. | 600/323 |
| 5,165,407 A | 11/1992 | Wilson et al. | |
| 5,238,729 A | 8/1993 | Debe | |
| 5,246,867 A | 9/1993 | Lakowicz et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,279,294 A | 1/1994 | Anderson et al. | |
| 5,285,792 A | 2/1994 | Sjoquist et al. | |
| 5,293,877 A | 3/1994 | O'Hara et al. | |
| 5,299,571 A | 4/1994 | Mastrototaro | |
| 5,320,725 A | 6/1994 | Gregg et al. | |
| 5,322,063 A | 6/1994 | Allen et al. | |
| 5,340,722 A | 8/1994 | Wolfbeis et al. | |
| 5,342,789 A | 8/1994 | Chick et al. | |
| 5,356,786 A | 10/1994 | Heller et al. | |
| 5,360,404 A | 11/1994 | Novacek et al. | |
| 5,372,427 A | 12/1994 | Padovani et al. | |
| 5,379,238 A | 1/1995 | Stark | |
| 5,390,671 A | 2/1995 | Lord et al. | |
| 5,391,250 A | 2/1995 | Cheney, II et al. | |
| 5,408,999 A | 4/1995 | Singh et al. | |
| 5,411,647 A | 5/1995 | Johnson et al. | |
| 5,431,160 A | 7/1995 | Wilkins | |
| 5,431,921 A | 7/1995 | Thombre | |
| 5,462,645 A | 10/1995 | Albery et al. | |
| 5,472,317 A | 12/1995 | Field et al. | |
| 5,489,414 A | 2/1996 | Schreiber et al. | |
| 5,497,772 A | 3/1996 | Schulman et al. | |
| 5,507,288 A | 4/1996 | Bocker et al. | |
| 5,509,410 A | 4/1996 | Hill et al. | |
| 5,514,718 A | 5/1996 | Lewis et al. | |
| 5,531,878 A | 7/1996 | Vadgama et al. | |
| 5,568,806 A | 10/1996 | Cheney, II et al. | |
| 5,569,186 A | 10/1996 | Lord et al. | |
| 5,582,184 A | 12/1996 | Erickson et al. | |
| 5,584,813 A | 12/1996 | Livingston et al. | |
| 5,586,553 A | 12/1996 | Halili et al. | |
| 5,593,852 A | 1/1997 | Heller et al. | |
| 5,601,435 A | 2/1997 | Quy | |
| 5,609,575 A | 3/1997 | Larson et al. | |
| 5,628,310 A | 5/1997 | Rao et al. | |
| 5,632,557 A | 5/1997 | Simons | |
| 5,653,239 A | 8/1997 | Pompei et al. | |
| 5,665,222 A | 9/1997 | Heller et al. | |
| 5,711,001 A | 1/1998 | Bussan et al. | |
| 5,711,861 A | 1/1998 | Ward et al. | |
| 5,733,044 A | 3/1998 | Rose et al. | |
| 5,735,285 A | 4/1998 | Albert et al. | |
| 5,749,656 A | 5/1998 | Boehm et al. | |
| 5,766,131 A | 6/1998 | Kondo et al. | |
| 5,772,586 A | 6/1998 | Heinonen et al. | |
| 5,791,344 A | 8/1998 | Schulman et al. | |
| 5,807,375 A | 9/1998 | Gross et al. | |
| 5,851,197 A | 12/1998 | Marano et al. | |
| 5,899,855 A | 5/1999 | Brown | |
| 5,925,021 A | 7/1999 | Castellano et al. | |
| 5,942,979 A | 8/1999 | Luppino | |
| 5,948,006 A | 9/1999 | Mann | |
| 5,957,854 A * | 9/1999 | Besson et al. | 600/509 |
| 5,961,451 A | 10/1999 | Reber et al. | |
| 5,964,993 A | 10/1999 | Blubaugh, Jr. et al. | |
| 5,965,380 A | 10/1999 | Heller et al. | |
| 5,971,922 A | 10/1999 | Arita et al. | |
| 5,995,860 A | 11/1999 | Sun et al. | |
| 6,001,067 A | 12/1999 | Shults et al. | |
| 6,022,368 A | 2/2000 | Gavronsky et al. | |
| 6,024,699 A | 2/2000 | Surwit et al. | |
| 6,026,321 A * | 2/2000 | Miyata et al. | 600/546 |
| 6,027,459 A | 2/2000 | Shain et al. | |
| 6,049,727 A | 4/2000 | Crothall | |
| 6,068,399 A | 5/2000 | Tseng | |
| 6,083,710 A | 7/2000 | Heller et al. | |
| 6,088,608 A | 7/2000 | Schulman et al. | |
| 6,091,975 A * | 7/2000 | Daddona et al. | 600/345 |
| 6,091,976 A | 7/2000 | Pfeiffer et al. | |
| 6,093,172 A | 7/2000 | Funderburk et al. | |
| 6,103,033 A | 8/2000 | Say et al. | |
| 6,117,290 A | 9/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,121,611 A | 9/2000 | Lindsay et al. | |
| 6,122,351 A | 9/2000 | Schlueter, Jr. et al. | |
| 6,134,461 A | 10/2000 | Say et al. | |
| 6,159,147 A | 12/2000 | Lichter et al. | |
| 6,162,611 A | 12/2000 | Heller et al. | |
| 6,175,752 B1 | 1/2001 | Say et al. | |
| 6,200,265 B1 | 3/2001 | Walsh et al. | |
| 6,212,416 B1 | 4/2001 | Ward et al. | |
| 6,219,574 B1 | 4/2001 | Cormier et al. | |
| 6,248,067 B1 | 6/2001 | Causey, III et al. | |
| 6,254,536 B1 | 7/2001 | DeVito | |
| 6,275,717 B1 | 8/2001 | Gross et al. | |
| 6,283,761 B1 | 9/2001 | Joao | |
| 6,283,982 B1 | 9/2001 | Levaughn et al. | |
| 6,284,478 B1 | 9/2001 | Heller et al. | |
| 6,293,925 B1 | 9/2001 | Safabash et al. | |
| 6,295,506 B1 | 9/2001 | Heinonen et al. | |
| 6,306,104 B1 | 10/2001 | Cunningham et al. | |
| 6,309,884 B1 | 10/2001 | Cooper et al. | |
| 6,329,161 B1 | 12/2001 | Heller et al. | |
| 6,348,640 B1 | 2/2002 | Navot et al. | |
| 6,359,444 B1 | 3/2002 | Grimes | |
| 6,360,888 B1 | 3/2002 | McIvor et al. | |
| 6,366,794 B1 | 4/2002 | Moussy et al. | |
| 6,368,141 B1 | 4/2002 | Van Antwerp et al. | |
| 6,377,828 B1 | 4/2002 | Chaiken et al. | |
| 6,379,301 B1 | 4/2002 | Worthington et al. | |
| 6,424,847 B1 | 7/2002 | Mastrototaro et al. | |
| 6,427,088 B1 | 7/2002 | Bowman, IV et al. | |
| 6,437,679 B1 | 8/2002 | Roques | |
| 6,440,068 B1 | 8/2002 | Brown et al. | |
| 6,478,736 B1 | 11/2002 | Mault | |
| 6,484,046 B1 | 11/2002 | Say et al. | |
| 6,514,718 B2 | 2/2003 | Heller et al. | |
| 6,520,326 B2 | 2/2003 | McIvor et al. | |
| 6,522,927 B1 | 2/2003 | Bishay et al. | |
| 6,551,494 B1 | 4/2003 | Heller et al. | |
| 6,558,320 B1 | 5/2003 | Causey, III et al. | |
| 6,558,321 B1 | 5/2003 | Burd et al. | |
| 6,560,471 B1 | 5/2003 | Heller et al. | |
| 6,561,978 B1 | 5/2003 | Conn et al. | |
| 6,562,001 B2 | 5/2003 | Lebel et al. | |
| 6,564,105 B2 | 5/2003 | Starkweather et al. | |

| | | |
|---|---|---|
| 6,565,509 B1 | 5/2003 | Plante et al. |
| 6,571,128 B2 | 5/2003 | Lebel et al. |
| 6,572,566 B2 | 6/2003 | Effenhauser |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,676,290 B1 | 1/2004 | Lu |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,849,052 B2 | 2/2005 | Uchigaki et al. |
| 6,854,882 B2 | 2/2005 | Chen |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman IV et al. |
| 6,958,705 B2 | 10/2005 | Lebel et al. |
| 6,959,211 B2 * | 10/2005 | Rule et al. ............. 600/310 |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,335,294 B2 | 2/2008 | Heller et al. |
| 7,340,309 B2 | 3/2008 | Miazga et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,416,541 B2 * | 8/2008 | Yuzhakov et al. ........... 604/272 |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,666,149 B2 | 2/2010 | Simons et al. |
| 7,711,402 B2 | 5/2010 | Shults et al. |
| 7,713,574 B2 | 5/2010 | Brister et al. |
| 7,715,893 B2 | 5/2010 | Kamath et al. |
| 2002/0013538 A1 * | 1/2002 | Teller ........... 600/549 |
| 2002/0019022 A1 | 2/2002 | Dunn et al. |
| 2002/0022855 A1 | 2/2002 | Bobroff et al. |
| 2002/0023852 A1 | 2/2002 | McIvor et al. |
| 2002/0042090 A1 | 4/2002 | Heller et al. |
| 2002/0082487 A1 * | 6/2002 | Kollias et al. ............... 600/316 |
| 2002/0103499 A1 | 8/2002 | Perez et al. |
| 2002/0106709 A1 | 8/2002 | Potts et al. |
| 2002/0119711 A1 | 8/2002 | VanAntwerp et al. |
| 2002/0128594 A1 | 9/2002 | Das et al. |
| 2002/0161288 A1 | 10/2002 | Shin et al. |
| 2002/0165462 A1 | 11/2002 | Westbrook et al. |
| 2002/0198444 A1 | 12/2002 | Uchigaki et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0065308 A1 * | 4/2003 | Lebel et al. ............... 604/891.1 |
| 2003/0069510 A1 * | 4/2003 | Semler ............... 600/509 |
| 2003/0078481 A1 | 4/2003 | McIvor et al. |
| 2003/0097092 A1 | 5/2003 | Flaherty |
| 2003/0100040 A1 | 5/2003 | Bonnecaze et al. |
| 2003/0109775 A1 | 6/2003 | O'Neil et al. |
| 2003/0134347 A1 | 7/2003 | Heller et al. |
| 2003/0144581 A1 | 7/2003 | Conn et al. |
| 2003/0144608 A1 | 7/2003 | Kojima et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0199910 A1 | 10/2003 | Boecker et al. |
| 2003/0212379 A1 | 11/2003 | Bylund et al. |

| | | | | | | |
|---|---|---|---|---|---|---|
| 2003/0217966 A1 | 11/2003 | Tapsak et al. | | 2006/0036139 A1 | 2/2006 | Brister et al. |
| 2004/0010207 A1 | 1/2004 | Flaherty et al. | | 2006/0036140 A1 | 2/2006 | Brister et al. |
| 2004/0011671 A1 | 1/2004 | Shults et al. | | 2006/0036141 A1 | 2/2006 | Kamath et al. |
| 2004/0040840 A1 | 3/2004 | Mao et al. | | 2006/0036142 A1 | 2/2006 | Brister et al. |
| 2004/0045879 A1 | 3/2004 | Shults et al. | | 2006/0036143 A1 | 2/2006 | Brister et al. |
| 2004/0054263 A1 | 3/2004 | Moerman et al. | | 2006/0036144 A1 | 2/2006 | Brister et al. |
| 2004/0064068 A1 | 4/2004 | DeNuzzio et al. | | 2006/0036145 A1* | 2/2006 | Brister et al. ............... 600/345 |
| 2004/0106858 A1 | 6/2004 | Say et al. | | 2006/0166629 A1 | 7/2006 | Reggiardo |
| 2004/0106859 A1 | 6/2004 | Say et al. | | 2006/0173444 A1 | 8/2006 | Choy et al. |
| 2004/0122353 A1 | 6/2004 | Shahmirian et al. | | 2006/0189863 A1 | 8/2006 | Peyser et al. |
| 2004/0133164 A1* | 7/2004 | Funderburk et al. ......... 604/134 | | 2006/0195029 A1 | 8/2006 | Shults et al. |
| 2004/0135684 A1 | 7/2004 | Steinthal et al. | | 2006/0200970 A1 | 9/2006 | Brister et al. |
| 2004/0138588 A1 | 7/2004 | Saikley et al. | | 2006/0222566 A1 | 10/2006 | Brauker et al. |
| 2004/0152622 A1 | 8/2004 | Keith et al. | | 2006/0226985 A1 | 10/2006 | Goodnow et al. |
| 2004/0167801 A1 | 8/2004 | Say et al. | | 2006/0247508 A1 | 11/2006 | Fennell |
| 2004/0171921 A1 | 9/2004 | Say et al. | | 2006/0258929 A1 | 11/2006 | Goode, Jr. et al. |
| 2004/0176672 A1 | 9/2004 | Silver et al. | | 2007/0016381 A1 | 1/2007 | Kamath et al. |
| 2004/0186362 A1 | 9/2004 | Brauker et al. | | 2007/0027381 A1 | 2/2007 | Stafford |
| 2004/0186365 A1 | 9/2004 | Jin et al. | | 2007/0060814 A1 | 3/2007 | Stafford |
| 2004/0193090 A1 | 9/2004 | Lebel et al. | | 2007/0073129 A1 | 3/2007 | Shah et al. |
| 2004/0199059 A1 | 10/2004 | Brauker et al. | | 2007/0078321 A1 | 4/2007 | Mazza et al. |
| 2004/0204687 A1 | 10/2004 | Mogensen et al. | | 2007/0078322 A1 | 4/2007 | Stafford |
| 2004/0225338 A1 | 11/2004 | Lebel et al. | | 2007/0106135 A1 | 5/2007 | Sloan et al. |
| 2004/0236200 A1 | 11/2004 | Say et al. | | 2007/0149875 A1 | 6/2007 | Ouyang et al. |
| 2004/0236251 A1 | 11/2004 | Roe et al. | | 2007/0163880 A1 | 7/2007 | Woo et al. |
| 2004/0254433 A1 | 12/2004 | Bandis et al. | | 2007/0173706 A1 | 7/2007 | Neinast et al. |
| 2004/0254434 A1 | 12/2004 | Goodnow et al. | | 2007/0191701 A1 | 8/2007 | Feldman et al. |
| 2004/0267300 A1 | 12/2004 | Mace | | 2007/0203407 A1 | 8/2007 | Hoss et al. |
| 2005/0003470 A1 | 1/2005 | Nelson et al. | | 2007/0203966 A1 | 8/2007 | Brauker et al. |
| 2005/0004494 A1 | 1/2005 | Perez et al. | | 2007/0235331 A1 | 10/2007 | Simpson et al. |
| 2005/0010269 A1 | 1/2005 | Lebel et al. | | 2007/0244398 A1* | 10/2007 | Lo et al. ..................... 600/500 |
| 2005/0027177 A1 | 2/2005 | Shin et al. | | 2007/0249922 A1 | 10/2007 | Peyser et al. |
| 2005/0031689 A1 | 2/2005 | Shults et al. | | 2008/0009692 A1 | 1/2008 | Stafford |
| 2005/0043598 A1 | 2/2005 | Goode, Jr. et al. | | 2008/0017522 A1 | 1/2008 | Heller et al. |
| 2005/0070819 A1 | 3/2005 | Poux et al. | | 2008/0021666 A1 | 1/2008 | Goode, Jr. et al. |
| 2005/0085872 A1* | 4/2005 | Yanagihara et al. ............ 607/60 | | 2008/0029391 A1 | 2/2008 | Mao et al. |
| 2005/0090607 A1 | 4/2005 | Tapsak et al. | | 2008/0033254 A1 | 2/2008 | Kamath et al. |
| 2005/0112169 A1 | 5/2005 | Brauker et al. | | 2008/0033268 A1 | 2/2008 | Stafford |
| 2005/0114068 A1 | 5/2005 | Chey et al. | | 2008/0039702 A1 | 2/2008 | Hayter et al. |
| 2005/0121322 A1 | 6/2005 | Say et al. | | 2008/0045824 A1 | 2/2008 | Tapsak et al. |
| 2005/0131346 A1 | 6/2005 | Douglas | | 2008/0071156 A1 | 3/2008 | Brister et al. |
| 2005/0143635 A1 | 6/2005 | Kamath et al. | | 2008/0083617 A1 | 4/2008 | Simpson et al. |
| 2005/0154410 A1 | 7/2005 | Conway et al. | | 2008/0086042 A1 | 4/2008 | Brister et al. |
| 2005/0176136 A1 | 8/2005 | Burd et al. | | 2008/0086044 A1 | 4/2008 | Brister et al. |
| 2005/0182306 A1 | 8/2005 | Sloan | | 2008/0086273 A1 | 4/2008 | Shults et al. |
| 2005/0187720 A1 | 8/2005 | Goode, Jr. et al. | | 2008/0097246 A1 | 4/2008 | Stafford |
| 2005/0192557 A1 | 9/2005 | Brauker et al. | | 2008/0108942 A1 | 5/2008 | Brister et al. |
| 2005/0195930 A1 | 9/2005 | Spital et al. | | 2008/0114280 A1 | 5/2008 | Stafford |
| 2005/0197554 A1* | 9/2005 | Polcha ....................... 600/365 | | 2008/0119707 A1 | 5/2008 | Stafford |
| 2005/0199494 A1 | 9/2005 | Say et al. | | 2008/0183061 A1 | 7/2008 | Goode, Jr. et al. |
| 2005/0203360 A1 | 9/2005 | Brauker et al. | | 2008/0183399 A1 | 7/2008 | Goode, Jr. et al. |
| 2005/0222518 A1 | 10/2005 | Dib | | 2008/0188731 A1 | 8/2008 | Brister et al. |
| 2005/0239154 A1 | 10/2005 | Feldman et al. | | 2008/0189051 A1 | 8/2008 | Goode, Jr. et al. |
| 2005/0239156 A1 | 10/2005 | Drucker et al. | | 2008/0194935 A1 | 8/2008 | Brister et al. |
| 2005/0241957 A1 | 11/2005 | Mao et al. | | 2008/0194936 A1 | 8/2008 | Goode, Jr. et al. |
| 2005/0245795 A1 | 11/2005 | Goode, Jr. et al. | | 2008/0194937 A1 | 8/2008 | Goode, Jr. et al. |
| 2005/0245799 A1 | 11/2005 | Brauker et al. | | 2008/0194938 A1 | 8/2008 | Brister et al. |
| 2005/0277164 A1 | 12/2005 | Drucker et al. | | 2008/0195232 A1 | 8/2008 | Carr-Brendel et al. |
| 2005/0287620 A1 | 12/2005 | Heller et al. | | 2008/0195967 A1 | 8/2008 | Goode, Jr. et al. |
| 2006/0001538 A1 | 1/2006 | Kraft et al. | | 2008/0197024 A1 | 8/2008 | Simpson et al. |
| 2006/0004303 A1 | 1/2006 | Weidenhaupt et al. | | 2008/0200788 A1 | 8/2008 | Brister et al. |
| 2006/0010098 A1 | 1/2006 | Goodnow et al. | | 2008/0200789 A1 | 8/2008 | Brister et al. |
| 2006/0015020 A1 | 1/2006 | Neale et al. | | 2008/0200791 A1 | 8/2008 | Simpson et al. |
| 2006/0015024 A1 | 1/2006 | Brister et al. | | 2008/0200897 A1 | 8/2008 | Hoss et al. |
| 2006/0016700 A1 | 1/2006 | Brister et al. | | 2008/0208025 A1 | 8/2008 | Shults et al. |
| 2006/0019327 A1 | 1/2006 | Brister et al. | | 2008/0214915 A1 | 9/2008 | Brister et al. |
| 2006/0020186 A1 | 1/2006 | Brister et al. | | 2008/0214918 A1 | 9/2008 | Brister et al. |
| 2006/0020187 A1 | 1/2006 | Brister et al. | | 2008/0228051 A1 | 9/2008 | Shults et al. |
| 2006/0020188 A1 | 1/2006 | Kamath et al. | | 2008/0228054 A1 | 9/2008 | Shults et al. |
| 2006/0020189 A1 | 1/2006 | Brister et al. | | 2008/0242961 A1 | 10/2008 | Brister et al. |
| 2006/0020190 A1 | 1/2006 | Kamath et al. | | 2008/0262469 A1 | 10/2008 | Brister et al. |
| 2006/0020191 A1* | 1/2006 | Brister et al. ............... 600/345 | | 2008/0275313 A1 | 11/2008 | Brister et al. |
| 2006/0020192 A1 | 1/2006 | Brister et al. | | 2008/0287764 A1 | 11/2008 | Rasdal et al. |

| | | |
|---|---|---|
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0099436 A1 | 4/2009 | Brister et al. |
| 2009/0102678 A1 | 4/2009 | Mazza et al. |
| 2009/0105569 A1 | 4/2009 | Stafford |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |

FOREIGN PATENT DOCUMENTS

| | | |
|---|---|---|
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1177802 | 6/2002 |
| EP | 2060284 | 5/2009 |
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-2004/061420 | 7/2004 |
| WO | WO-2005/089103 | 9/2005 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/120363 | 10/2007 |
| WO | WO-2007/143225 | 12/2007 |
| WO | WO-2008/031106 | 3/2008 |
| WO | WO-2008/031110 | 3/2008 |
| WO | WO-2008/039944 | 4/2008 |
| WO | WO-2008/051920 | 5/2008 |
| WO | WO-2008/051924 | 5/2008 |
| WO | WO-2008/103620 | 8/2008 |
| WO | WO-2008/150917 | 12/2008 |
| WO | WO-2009/062675 | 5/2009 |

OTHER PUBLICATIONS

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technolgy & Therapeutics*, vol. 5, No. 5, 2003, pp. 769-779.

Johnson, P. C., "Peripheral Circulation", *John Wiley & Sons*, 1978, pp. 198.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensor: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Contructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

International Search Report and Written Opinion of the International Searching Authority for PCT Application No. PCT/US2006/037928 filed Sep. 28, 2006 to Abbott Diabetes Care, Inc., mailed Jul. 11, 2008.

European Application No. EP-06815715.5, Extended European Search Report mailed Oct. 30, 2009.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Jungheim, K., et al., "How Rapid Does Glucose Concentration Change in Daily Life of Patients with Type 1 Diabetes?", 2002, pp. 250.

McGarraugh, G., et al., "Glucose Measurements Using Blood Extracted from the Forearm and the Finger", *TheraSense, Inc.*, 2001, 16 pages.

Aussedat, B., et al., "A User-Friendly Method for Calibrating a Subcutaneous Glucose Sensor-Based Hypoglycaemic Alarm", *Biosensors & Bioelectronics*, vol. 12, No. 11, 1997, pp.1061-1071.

Schmidt, F. J., et al., "Calibration of a Wearable Glucose Sensor", *The International Journal of Artificial Organs*, vol. 15, No. 1, 1992, pp. 55-61.

European Application No. EP-06815715.5, Official Letter from European Patent Office mailed Feb. 9, 2010.

PCT Application No. PCT/US2006/037928, International Preliminary Report on Patentability and Written Opinion of the International Searching Authority mailed Mar. 19, 2009.

Reexamination U.S. Appl. No. 90/008,172, Request for Reexamination of U.S. Patent No. 6,990,366, filed Aug. 16, 2006.

Reexamination U.S. Appl. No. 90/008,457, Request for Reexamination of U.S. Patent No. 6,990,366, filed Jan. 23, 2007.

Reexamination U.S. Appl. No. 90/009,104, Request for Reexamination of U.S. Patent No. 6,990,366, filed Apr. 8, 2008.

Reexamination U.S. Appl. No. 90/009,328, Request for Reexamination of U.S. Patent No. 6,990,366, filed Nov. 10, 2008.

Reexamination U.S. Appl. No. 90/010,791, Request for Reexamination of U.S. Patent No. 6,990,366, filed Dec. 22, 2009.

\* cited by examiner

INTEGRATED TRANSMITTER UNIT AND SENSOR INTRODUCER MECHANISM AND METHODS OF USE

BACKGROUND

Continuous glucose monitoring systems generally include a sensor such as a subcutaneous analyte sensor, at least a portion of which is configured for fluid contact with biological fluid, for detecting analyte levels such as for example glucose or lactate levels, a transmitter (such as for example an RF transmitter) in communication with the sensor and configured to receive the sensor signals and to transmit them to a corresponding receiver unit by for example, using RF data transmission protocol. The receiver may be operatively coupled to a glucose monitor that performs glucose related calculations and data analysis.

The transmitter may be mounted or adhered to the skin of a patient and also in signal communication with the sensor. Generally, the sensor is configured to detect the analyte of the patient over a predetermined period of time, and the transmitter is configured to transmit the detected analyte information over the predetermined period of time for further analysis. To initially deploy the sensor so that the sensor contacts and electrodes are in fluid contact with the patient's analyte fluids, a separate deployment mechanism such as a sensor inserter or introducer is used. Moreover, a separate base component or mounting unit is provided on the skin of the patient so that the transmitter unit may be mounted thereon, and also, to establish signal communication between the transmitter unit and the analyte sensor.

As discussed above, the base component or mounting unit is generally adhered to the skin of the patient using an adhesive layer that is fixedly provided on the bottom surface of the base component or the mounting unit for the transmitter. To minimize data errors in the continuous or semi-continuous monitoring system, it is important to properly insert the sensor through the patient's skin and securely retain the sensor during the time that the sensor is configured to detect analyte levels. In addition to accurate positioning of the sensor through the skin of the patient, it is important to minimize the level of pain associated with the insertion of the sensor through the patient's skin.

Additionally, for the period of continuous or semi-continuous monitoring which can include, for example, 3 days, 5 days or 7 days, it is important to have the transmitter unit securely mounted to the patient, and more importantly, in proper contact with the analyte sensor so as to minimize the potential errors in the monitored data. Indeed, when mounted onto the skin using adhesives, bodily fluid such as sweat and muscle flexure may weaken the adhesive securing the transmitter unit onto the skin surface, and which may potentially cause the transmitter unit to detach from the skin prematurely.

In view of the foregoing, it would be desirable to have methods and apparatuses which would minimize the number of components that are needed for the patient to manipulate in order to deploy the sensor and the transmitter unit to properly be initialized and set-up so that the sensor may be configured to monitor a biological fluid to detect, for example, analyte levels of the patient and the transmitter unit may be configured to transmit data associated with the detected analyte levels of the patient. Further, it would be desirable to have methods and apparatuses that include an integrated sensor insertion mechanism and transmitter mount or housing portion which may be mounted on the patient's skin securely, with ease and relative little pain to the patient.

SUMMARY OF THE INVENTION

In certain embodiments, there is provided a method and apparatus for providing an integrated transmitter unit and sensor insertion mechanism. Embodiments may include a base portion (e.g., a flexible base portion) for securing the transmitter unit around a body part of the patient, such as the patient's arm or leg and including a detachable disposable sensor introducer providing a low profile integrated data monitoring system.

In this manner, in accordance with the various embodiments of the invention, there is provided an integrated transmitter unit and sensor insertion mechanism that is configured for a multi-use disposable monitoring components for use in continuous glucose monitoring systems. More specifically, several components such as the transmitter unit, the sensor, sensor insertion mechanism (including, for example, a pre-assembled sensor, introducer and protective housing combination) and the skin mounting units are integrated into fewer components (two or less, for example), to simplify the use thereof and also to provide additional ease of use to the patients.

Moreover, an integrated transmitter unit and sensor insertion mechanism of the subject invention may be configured to depart from the reliance upon an adhesive patch as the primary method of transmitter attachment to the patient so that the mounting of the transmitter to the patient is not substantially affected by the patient's bodily fluids, cosmetics, lotions, body hair, skin type/condition or any other factor that may potentially weaken the adhesive condition of an adhesive patch.

DETAILED DESCRIPTION

Figure 1A:
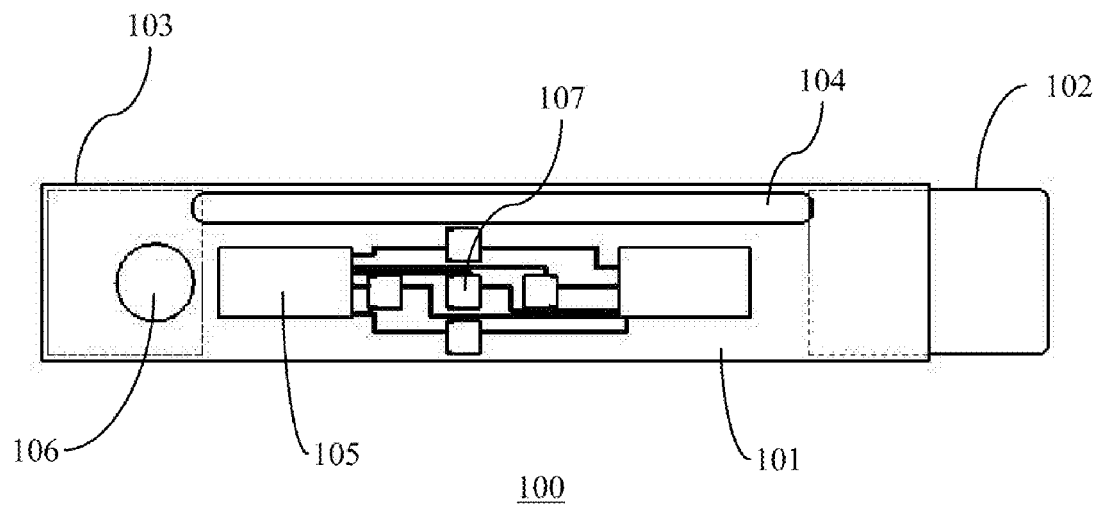
FIGS. 1A, 1B and 1C illustrate a top view, a bottom view, and a perspective view, respectively, of the integrated transmitter unit and sensor insertion mechanism for use in data monitoring system in accordance with one embodiment of the present invention.
Figure 1B:
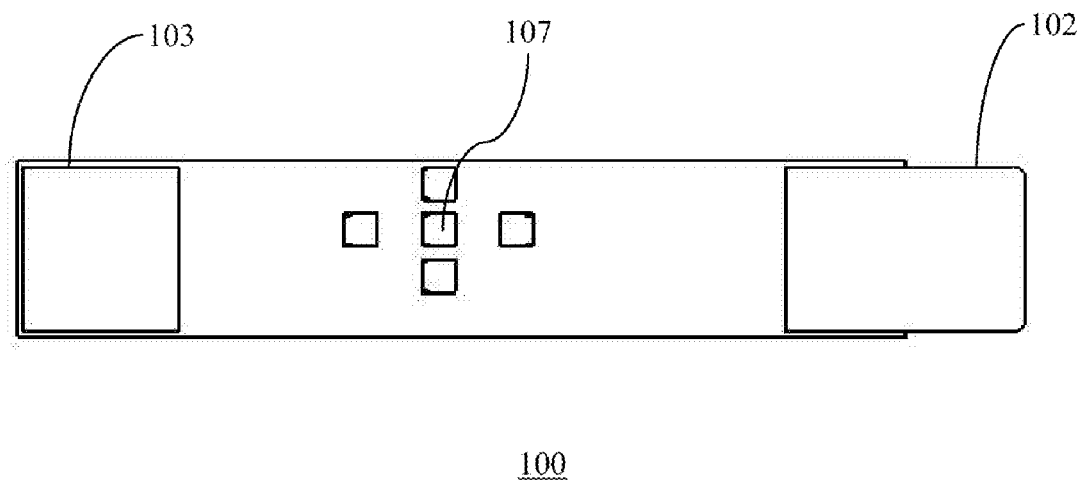
Figure 1C:
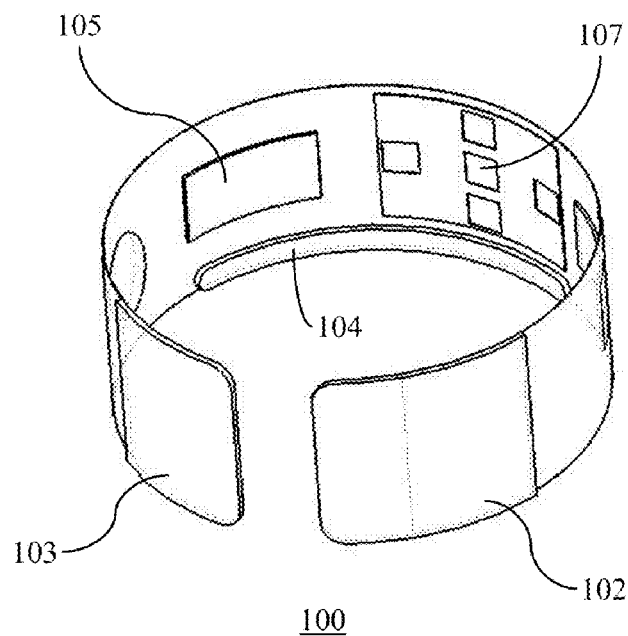

FIGS. 1A, 1B and 1C illustrate a top view, a bottom view, and a perspective view, respectively, of an integrated transmitter unit and sensor insertion mechanism for use in data monitoring system in accordance with one embodiment of the present invention. Referring to FIGS. 1A-1C, an integrated transmitter unit and sensor insertion mechanism 100 in one embodiment includes a substantially elongated and base portion 101, which base portion may be a flexible base portion. The base portion 101 is substantially shaped and configured in one embodiment to be of sufficient length to partially or completely wrap around the patient's arm, wrist, thigh, calf, torso or any other part of the patient's body where the sensor is to be positioned and introduced. In one embodiment, the base portion 101 may be made of a material that is pre-formed or molded by the patient, to follow the curvature of the anatomy, or may be made of a flexible form filling or conformable material such as fabric, strap or sleeve.

Referring back to FIGS. 1A-1C, in one embodiment of the present invention, there is provided a securing mechanism that includes parts 102 and 103 to the respective ends of the base portion 101 as shown in the Figure, which may be in the form of hook portion 102 and a loop portion 103. More specifically, in the embodiment including a Velcro-type securing mechanism, the hook portion 102 provided at a first end of the base portion 101 includes a Velcro hook which is configured to be mated with the Velcro loop at the loop portion 103 at the second end of the base portion 101. In this manner, the integrated transmitter unit and sensor insertion mechanism 100 may be securely and substantially fixedly positioned around the patient's arm, for example, using the Velcro mechanism provided thereon. Within the scope of the present invention, the hook portion 102 and the loop portion 103 may comprise any other suitable securing mechanism, including but not limited to, a buckle type securing system, a button type securing system, a hook or latch mechanism, and a zipper type fastening mechanism.

Referring again to FIGS. 1A-1C, the integrated transmitter unit and sensor insertion mechanism 100 in one embodiment is provided with the transmitter electronics 105 substantially embedded within the base material 101. Moreover, the transmitter electronics 105 is also configured to be in electrical communication with a transmitter antenna 104 (for example, an RF transmission antenna), as well as a power source 106 (for example, a disposable battery) that may also be provided substantially within the base material 101. In one embodiment, the integrated transmitter unit and sensor insertion mechanism 100 may be provided to the patient fully assembled with the power source 106, the transmitter antenna 104, and the transmitter electronics 105 embedded or laminated within the layers of the base material 101. In this manner, once positioned, the transmitter unit and sensor insertion mechanism 100 may be worn by the patient and may have a very low profile, with for example, approximately, 4-5 mm of thickness so as to advantageously minimize physical hindrance to the patient's daily activities while using the transmitter unit and sensor insertion mechanism 100. However, other dimensions are possible as well.

Referring still again to FIGS. 1A-1C, there is also shown a sensor insertion location 107 provided on the base material 101 of the integrated transmitter unit and sensor insertion mechanism 100. In this manner, during the insertion process, the patient is able to readily determine the proper location of sensor insertion so as to accurately and effectively deploy the sensor to be in signal communication with the transmitter unit electronics (for example, the corresponding contact points for the respective electrodes such a the working, reference, and counter (or reference/counter) electrodes of the sensor, and optionally, the guard trace of the sensor).

In the manner described above, in accordance with one embodiment of the present invention, the integrated transmitter unit and sensor insertion mechanism 100 is configured to depart from the reliance upon an adhesive patch as the primary method of transmitter attachment to the patient so that it is not substantially affected by the patient's bodily fluids, cosmetics, lotions, body hair, skin type/condition or any other factor that may potentially weaken the adhesive condition of the adhesive patch. Moreover, in one embodiment, the base material 101 of the integrated transmitter unit and sensor insertion mechanism 100 may be formulated to provide some measure of moisture vapor transmission rate (MVTR) to allow the patient's skin to breath or ventilate.

Figure 2:
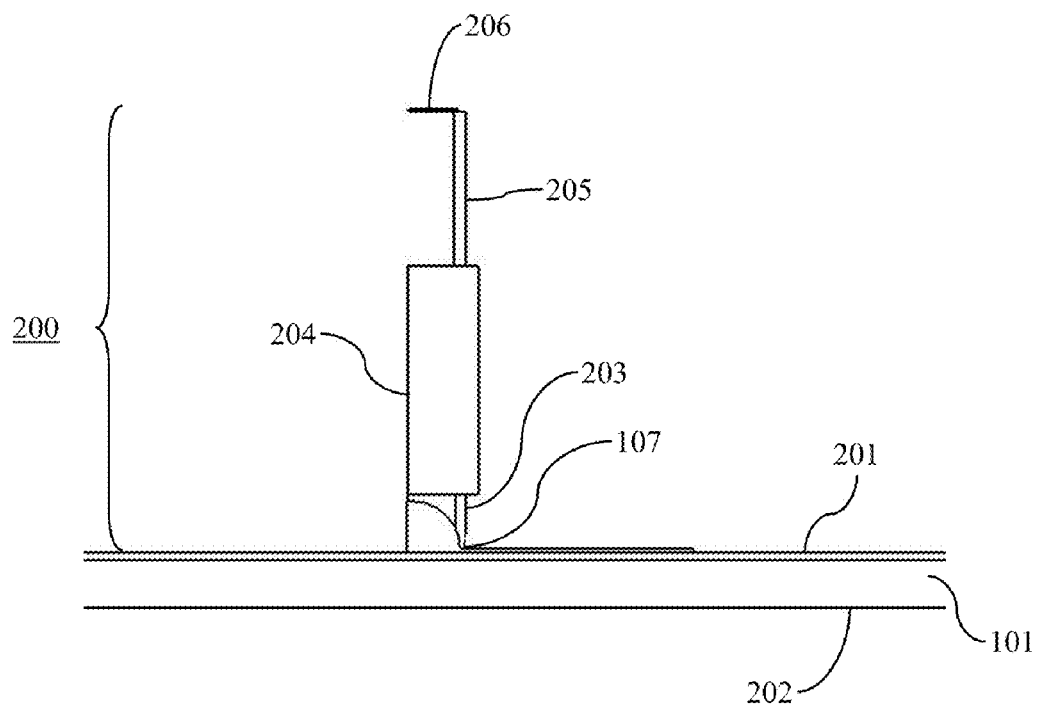
FIG. 2 illustrates a sensor introducer unit positioned relative to the integrated transmitter and sensor insertion mechanism in pre-deployment position in accordance with one embodiment of the present invention.

FIG. 2 illustrates a sensor introducer unit positioned relative to the integrated transmitter and sensor insertion mechanism in pre-deployment position in accordance with one embodiment of the present invention. Referring to FIG. 2, in one embodiment of the present invention, a sensor introducer assembly 200 is provided and includes an introducer mechanism 205 including a handle portion 206 configured for manipulation during manual (or otherwise) sensor insertion process. Also provided in the introducer mechanism 205 is a sensor casing 204 that is operatively coupled to the introducer mechanism 205 and which is configured to house a sensor (not shown) in physical cooperation with the introducer mechanism 205.

Referring back to FIG. 2, it can be seen that a tip portion 203 of the introducer mechanism 205 is substantially aligned with the sensor insertion location 107 on a top surface 201 of the base portion 101 of the integrated transmitter unit and sensor insertion mechanism 100. Moreover, it can be further seen from FIG. 2 that a bottom surface 202 of the base portion 101 of the integrated transmitter unit and sensor insertion mechanism 100 is in physical contact with the skin of the patient.

As will be described in further detail below, upon positioning the tip portion 203 of the introducer mechanism 205 substantially aligned with the sensor insertion position 107 on the base portion 101, the patient may depress upon the handle portion 206 of the introducer mechanism 205 so as to insert the analyte sensor transcutaneously such that at least a portion of the sensor is positioned to be in fluid contact with the patient's biological fluids, such as for example, interstitial fluids. Other manners of activating the introducer may be used within the scope of the present invention.

Thereafter, upon insertion and positioning the sensor, the handle portion 206 may be collapsed into the sensor casing 204, and the sensor casing 204 pivoted approximately 90 degrees substantially about the sensor insertion position 107, so as to collapse the sensor casing 204 onto the upper surface 201 of the base portion 101 of the integrated transmitter unit and sensor insertion mechanism 100 including the sensor electrical contact surface. In this manner, a low profile, substantially thin sensor and transmitter combination may be provided to the patient to be worn for a predetermined period of time, while minimizing potential interference with the patient's daily physical activities and securely holding the transmitter in place on the patient.

Figure 3A:
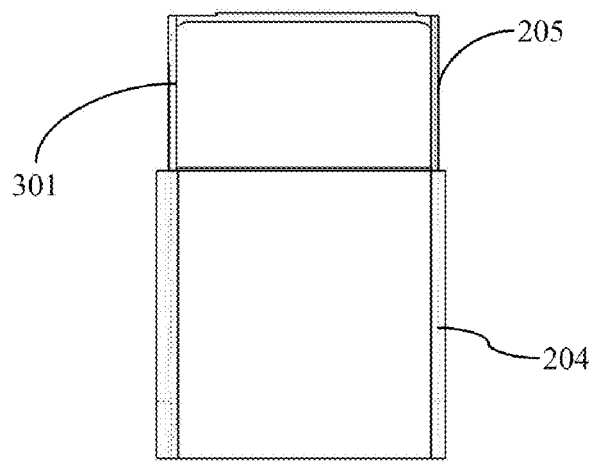
FIGS. 3A-3B illustrate a front planar view and a perspective view, respectively, of the sensor introducer mechanism in pre-deployment position in accordance with one embodiment of the present invention.
Figure 3B:
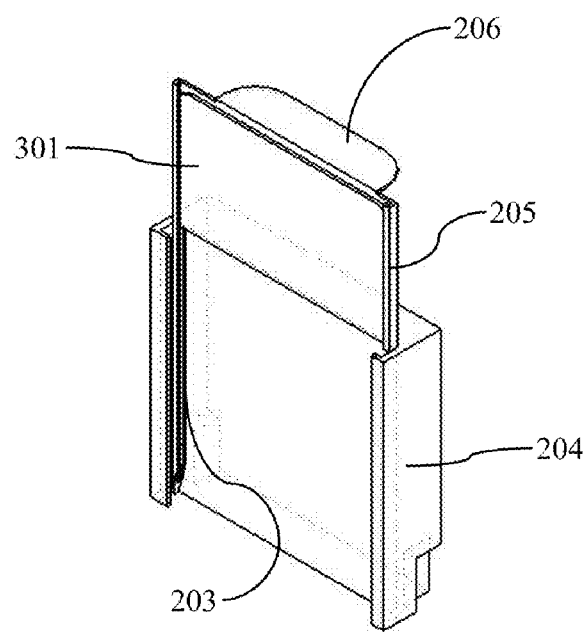

FIGS. 3A-3B illustrate a front planar view and a perspective view, respectively, of the sensor introducer mechanism in pre-deployment position in accordance with one embodiment of the present invention. Referring to FIGS. 3A-3B, it can be seen that the sensor 301 is provided substantially engaged with the introducer 205, a portion of each of which is guided within and through the inner section of the sensor casing 204. Moreover, the introducer tip portion 203 is configured to substantially contain the portion of the sensor 301 that is to be placed under the patient's skin, e.g., subcutaneously.

Figure 4A:
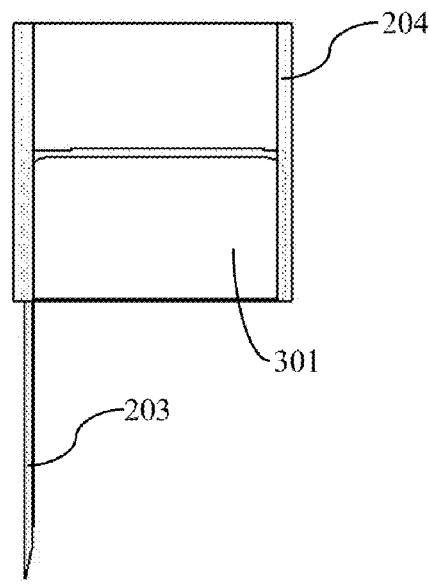
FIGS. 4A-4B illustrate a front planar view and a perspective view, respectively, of the sensor introducer mechanism in deployed position in accordance with one embodiment of the present invention.
Figure 4B:
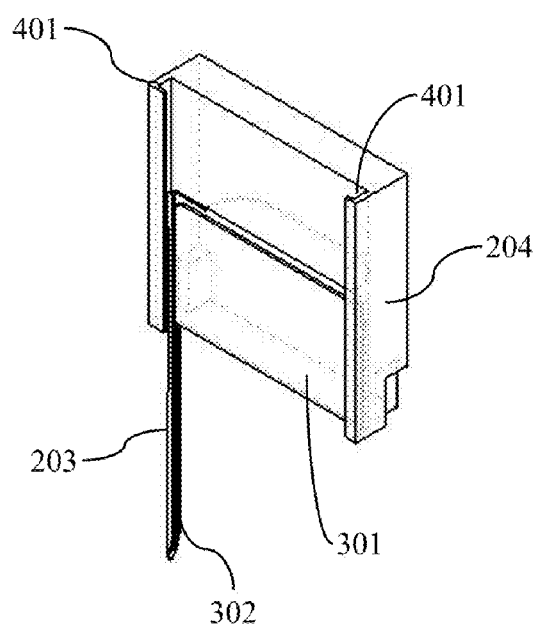

FIGS. 4A-4B illustrate a front planar view and a perspective view, respectively, of the sensor introducer mechanism in deployed position in accordance with one embodiment of the present invention. Referring to FIGS. 4A-4B, upon manual operation of the introducer handle portion 206, by the force applied by the patient thereonto, the introducer tip portion 203 is configured to guide a sensor tip 302 of the sensor 301 through the skin of the patient, so as to position at least a portion of the sensor tip 302 in fluid contact with the patient's biological fluids such as interstitial fluid. Moreover, it can be seen from FIG. 4B that the sensor casing 204 in one embodiment may be provided with one or more inner grooves 401 which are configured to substantially guide the movement of the introducer 305 and the sensor 301 through the sensor casing 204, and further, to provide substantially fixed support of the introducer 305 position relative to the sensor insertion position 107 during the operation of the introducer handle portion 206 to transcutaneously deploy the sensor 302.

Figure 5A:
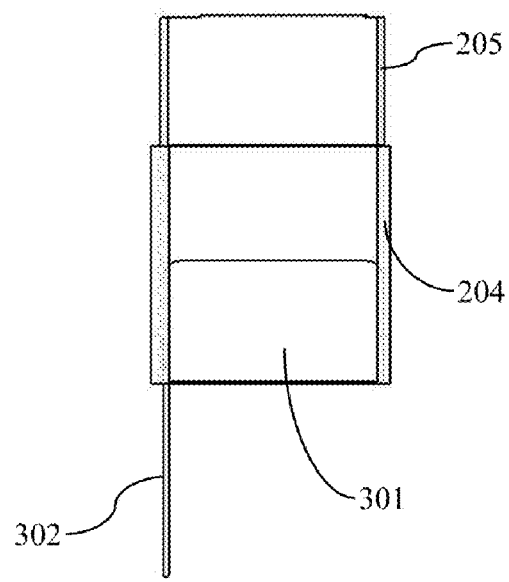
FIGS. 5A-5B illustrate front planar view and a perspective view, respectively, of the sensor introducer mechanism with the deployed sensor and the introducer in removal position, in accordance with one embodiment of the present invention.
Figure 5B:
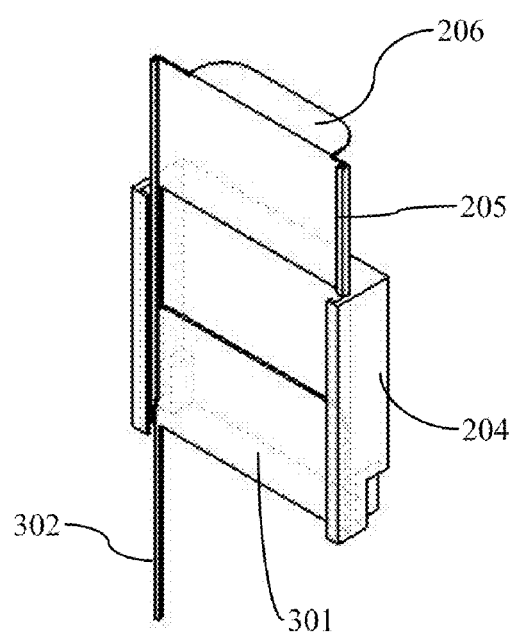

FIGS. 5A-5B illustrate front planar view and a perspective view, respectively, of the sensor introducer mechanism with the deployed sensor and the introducer in removal position, in accordance with one embodiment of the present invention. Referring to FIGS. 5A-5B, it can be seen that the handle portion 206 and the introducer 205 are protruded out of the sensor casing 204 upon sensor deployment.

More specifically, in one embodiment, after the patient applies pressure onto the handle portion 206 so as to deploy the sensor 301, the patient may retract or withdraw the introducer 205 from the deployed position, by retracting or pulling the handle portion 206 in the opposite direction of the sensor deployment direction. Alternatively, the introducer 205 may be provided with a spring bias mechanism or a similar mechanism which would allow the introducer 205 to be retracted substantially automatically after deployment of the sensor 301.

Referring back to FIGS. 5A-5B, after deployment of the sensor 301 and retraction of the introducer 205, the introducer 205 may be detached from the sensor casing 204 and discarded. Alternatively, the introducer 205 in a further embodiment may be configured and sized so as to be substantially and completely housed within the sensor casing 204 upon deployment of the sensor 301.

Figure 6:
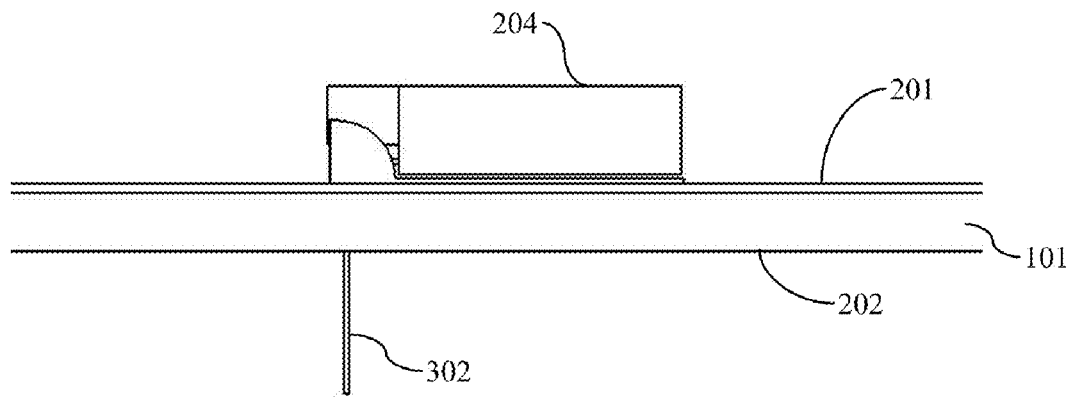
FIG. 6 illustrates the sensor introducer unit positioned relative to the integrated transmitter and sensor insertion mechanism in post sensor deployment position in accordance with one embodiment of the present invention.
Figure 7A:
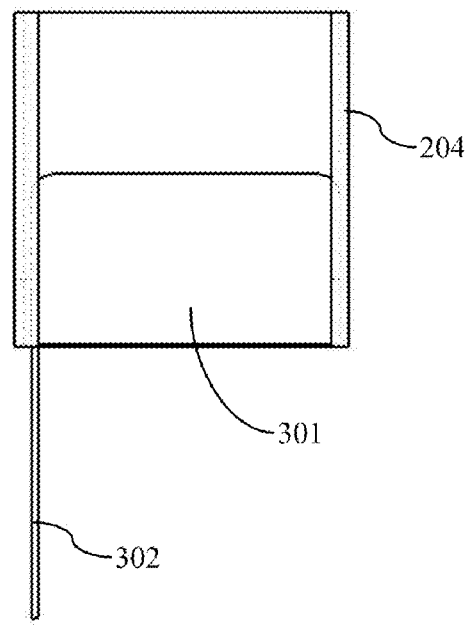
FIGS. 7A-7C illustrate a front planar view, a perspective view, and a side planar view, respectively of the deployed sensor with the introducer removed in accordance with one embodiment of the present invention.
Figure 7B:
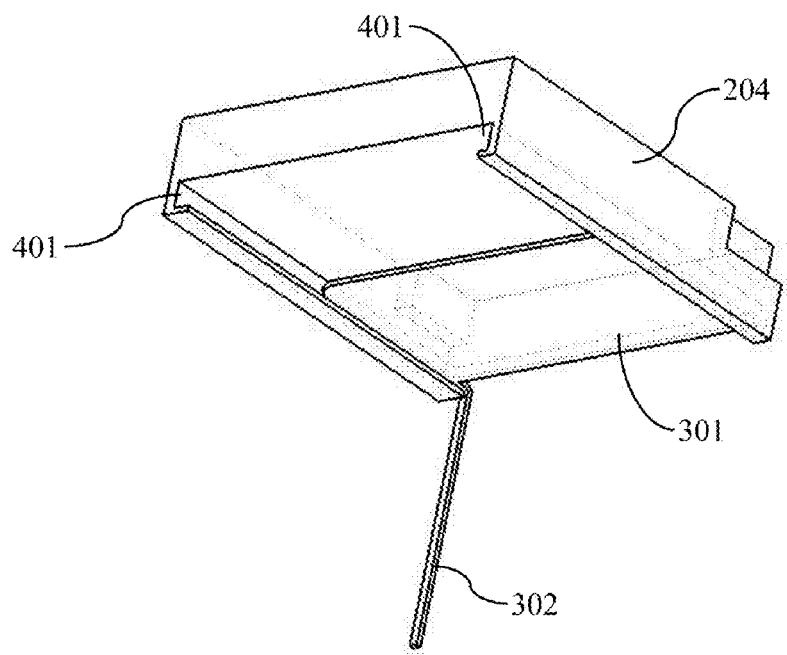
Figure 7C:
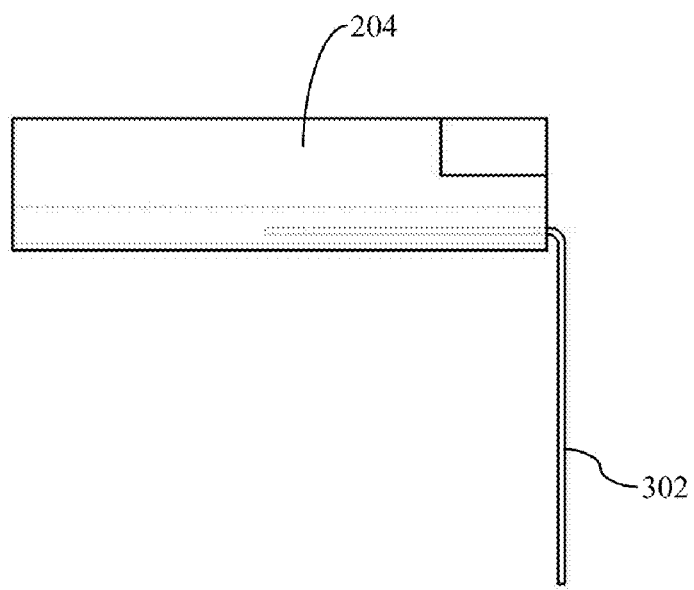

FIG. 6 illustrates the sensor introducer unit positioned relative to the integrated transmitter and sensor insertion mechanism in post sensor deployment position in accordance with one embodiment of the present invention. Moreover, FIGS. 7A-7C illustrate a front planar view, a perspective view, and a side planar view, respectively of the deployed sensor with the introducer removed in accordance with one embodiment of the present invention. Referring to the Figures, it can be seen that the sensor casing 204 may be provided in a locked and secure position on the upper surface 201 of the base portion 101 of the integrated transmitter unit and sensor insertion mechanism 100 such that a substantially low profile, sensor and transmitter system may be provided for extended wear and use by the patients to monitor one or more biological fluids and for transmission of data associated with the detected or monitored fluid to a receiver unit for further data processing, health management diagnosis and treatment.

Figure 8:
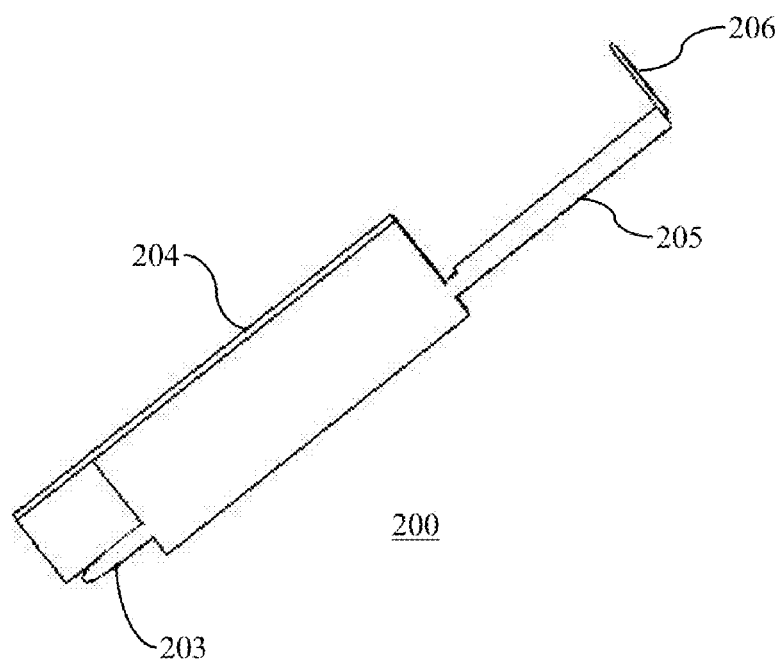
FIG. 8 illustrates an introducer assembly for used in angled sensor insertion in accordance with one embodiment of the present invention.
Figure 9:
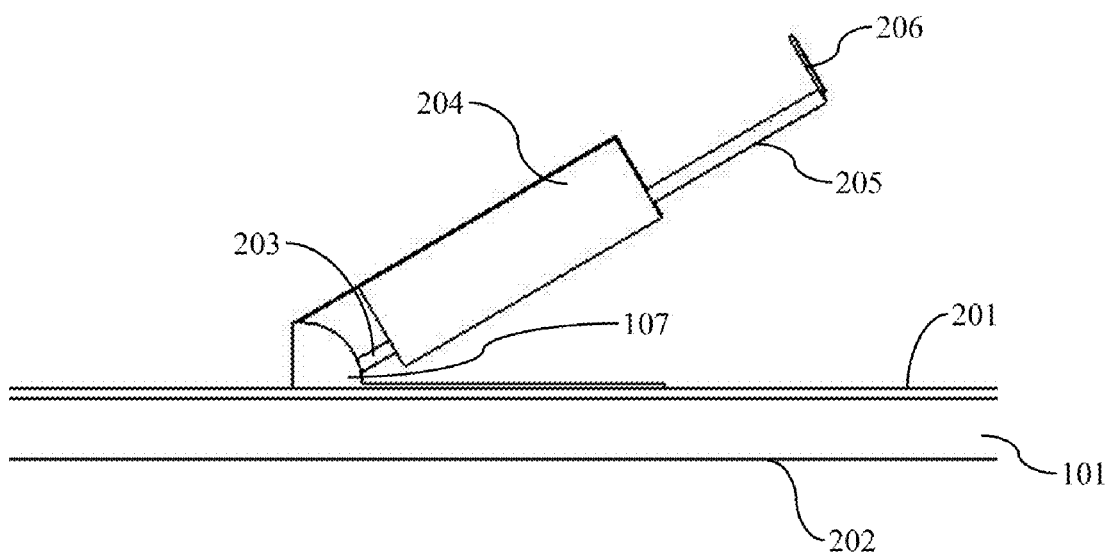
FIG. 9 illustrates a sensor introducer assembly positioned relative to the integrated transmitter and sensor insertion mechanism in pre-deployment position for angled insertion in accordance with one embodiment of the present invention.

FIG. 8 illustrates an introducer assembly for used in angled sensor insertion in accordance with one embodiment of the present invention, and FIG. 9 illustrates the sensor introducer assembly positioned relative to the integrated transmitter and sensor insertion mechanism in pre-deployment position for angled insertion in accordance with one embodiment of the present invention. It can be seen that for applications were the insertion is desirable at an angle other than about 90 degrees relative to the surface of the patient's skin, within the scope of the present invention, the sensor introducer assembly 200 may be configured to provide angled insertion for varying angles of sensor insertion, and which in turn, may correspondingly vary the depth at which the sensor tip 302 is positioned below the patient's skin and in fluid contact with the patient's biological fluids such as interstitial fluid in the subcutaneous space, or the like.

For example, it can be seen that given a substantially fixed length of the sensor tip 302, the greater the angle of the insertion (relative to the surface of the patient's skin), the deeper the position of the sensor tip 302 placed under the skin, and where the deepest position of subcutaneous placement of the sensor tip 302 is achieved substantially at about 90 degrees angle relative to the surface of the patient's skin, and as illustrated above in conjunction with the embodiment shown in FIG. 6.

Figure 10:
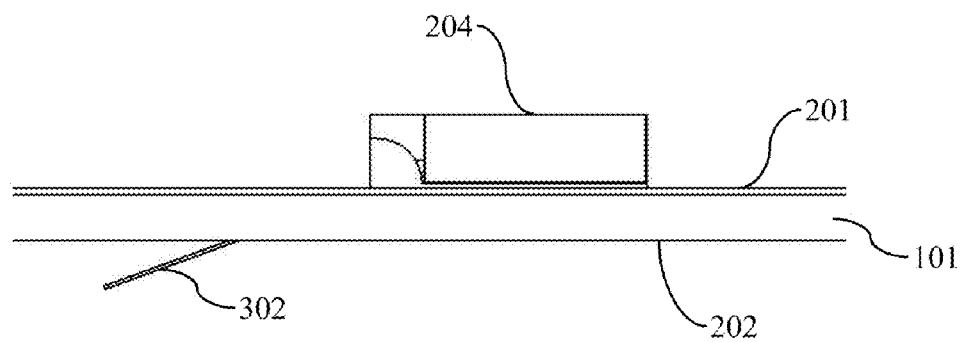
FIG. 10 illustrates the sensor introducer unit positioned relative to the integrated transmitter and sensor insertion mechanism in post sensor deployment position for angled insertion in accordance with one embodiment of the present invention.
Figure 11A:
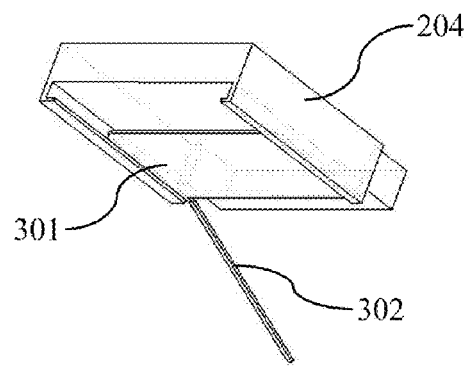
FIGS. 11A-11B illustrates perspective view and side planar view, respectively of the deployed sensor with the introducer removed for angled sensor insertion in accordance with one embodiment of the present invention.
Figure 11B:
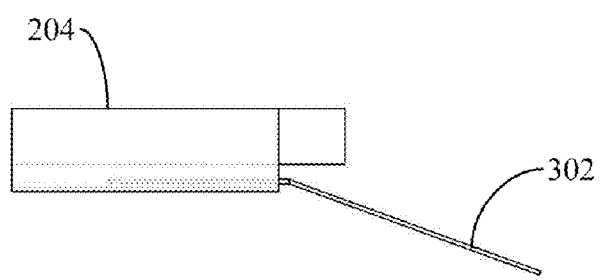

Additionally, FIG. 10 illustrates the sensor introducer unit positioned relative to the integrated transmitter and sensor insertion mechanism in post sensor deployment position for angled insertion, and FIGS. 11A-11B illustrates perspective view and side planar view, respectively of the deployed sensor with the introducer removed for angled sensor insertion in accordance with one embodiment of the present invention.

As discussed above, in accordance with the various embodiment of the present invention, the base portion 101 is placed on the patient such as around the patient's arm and secured in position using the securing mechanism, e.g., hook portion 102 and the loop portion 103. Within the scope of the present invention, other methods and devices for securing the base portion 101 may be used such as, for example, metal hooks, medical grade adhesive tape, elastic bands, or straps with buckles or any other equivalent methods or devices for securing the base portion 101 onto the patient.

The sensor casing 204 with the introducer 205 and the sensor 301, pre-assembled therein, may be placed on the base portion 101 so as to substantially align the introducer tip 203 with the sensor insertion position 107 of the base portion 101. While one sensor insertion position 107 is shown in the Figures, within the scope of the present invention, a plurality of sensor insertion positions may be provided on the upper surface 201 of the base portion 101. This would provide the additional convenience for the patients by providing several insertion site locations on the skin of the patient after the base portion 101 is substantially fixedly positioned on the patient's skin. Additionally, within the scope of the present invention, the base portion may be provided with a plurality of sensor insertion positions 107 such that the integrated transmitter unit and sensor insertion mechanism 100 may be configured for use with multiple sensors either concurrently or sequentially.

In one aspect of the present invention, the transmitter electronics 105 may be configured to selectively shut off or disable the electronics at the sensor insertion positions after the sensor 301 is in use for the prescribed period of time (for example, about 1 day, about 3 days, about 5 days, about 7 days or more, e.g., about 30 days or more). In this manner, it is possible to provide the additional safety precaution by preventing continued used of the integrated transmitter unit and sensor insertion mechanism 100 after a specified number of uses (corresponding to the number of the sensor insertion positions). This option may prevent the patients from multiple usage of the same sensor 301 rather than discarding after the initial usage, and also, for using the integrated transmitter unit and sensor insertion mechanism 100 beyond the recommended periods of usage frequency. Additionally, within the scope of the present invention, the power supply 106 may be provided with a low capacitor disposable battery so as to limit the life of the integrated transmitter unit and sensor insertion mechanism 100 once it has been activated.

In addition, within the scope of the present invention, the insertion process of the sensor 301 is described as performed manually by the patient. Alternatively, within the scope of the present invention, the insertion process of the sensor 301 may be configured with a semi-automated mechanism or a fully automated mechanism provided with an insertion trigger switch, for example. Moreover, within the scope of the present invention, angled insertion of the sensor 301 may be achieved by the design and orientation of the sensor casing 204 at the sensor insertion position 107.

Additionally, within the scope of the present invention, the physical dimensions of the sensor casing 204 and the orientation of the introducer 205 in cooperation with the sensor casing 204 may provide the desired sensor insertion depth, and also to control the ease of sensor deployment. Indeed, when the introducer 205 bottoms out at the sensor insertion position 107 within the sensor casing 204, the sensor depth or the below-the-skin position is determined to be reached, and thereafter, the introducer 205 may be safely discarded, for example, by detaching from the sensor casing 204 or substantially completely encasing within the sensor casing 204. Then, the sensor casing 204 may be rotatably pushed substantially about the sensor insertion position 107 so that it may be maintained in a locked position, thus holding the sensor 301 in place, and establishing electrical communication with the transmitter electronics 105 laminated, for example, within the base portion 101 of the integrated transmitter unit and sensor insertion mechanism 100. In one embodiment, the sensor casing 204 may be provided with a compressible seal around its perimeter to prevent moisture, particulate, and other foreign materials from contaminating the transmitter electronics 105 or potentially compromising the integrity of the electrical contacts and signal.

In this manner, the detected analyte levels from the sensor 301 may be provided to transmitter electronics 105, which is, in one embodiment, configured to wirelessly transmit data corresponding to the detected analyte levels from the sensor to a receiver unit via the antenna 104, where the receiver unit may include a glucose monitor unit and/or an insulin pump unit and/or a computer terminal, or any other electronic device capable of being configured for wireless (or other) communication. Within the scope of the present invention, the receiver unit functions may be integrated into portable electronic devices such as a watch, a pager, a mobile telephone, personal digital assistant, and the like. Additional information on the detection, monitoring and analysis of analyte levels are described in further detail in U.S. Pat. No. 6,175,752 entitled "Analyte Monitoring Device and Methods of Use" the disclosure of which is incorporated herein by reference for all purposes.

In a further embodiment, the transmitter electronics 105 may includes a wireless communication unit for wireless transmission of the signal, where the wireless communication unit may include one or more of a radio frequency (RF) communication unit, a Bluetooth communication unit, an infrared communication unit, an 801.11x communication unit, or a Zigbee communication unit. Similarly, the receiver unit may be configured to support one more or of the above-referenced wireless communication protocols to communicate with the transmitter unit.

In this manner, within the scope of the present invention, there is provided an integrated transmitter unit and sensor insertion mechanism that is configured for a multi-use disposable monitoring components for use in continuous glucose monitoring systems. More specifically, several components such as the transmitter unit, the sensor, sensor insertion mechanism (including, for example, a pre-assembled sensor, introducer and protective housing combination) and the skin mounting units are integrated into fewer components (two or less, for example), to simplify the use and also to provide additional ease of use to the patients.

Accordingly, within the scope of the present invention, it is possible to eliminate the separate system components of the skin attachment system, sensor insertion and the transmitter unit along with the associated safety precautions, material costs, weight, packaging, handling, disposal, and attaching to the skin patch. Furthermore, a low profile integrated system may be provided that would substantially minimize potential interference with the patient's normal daily activities. In the embodiments described above, while the handle portion 206 (FIG. 2) for example, is configured to be discarded after the sensor insertion process, within the scope of the present invention, the handle portion of the sensor introducer assembly may be configured to be integrated within the sensor introducer assembly—for example, within the sensor casing 204.

Moreover, the integrated transmitter unit and sensor insertion mechanism 100 may be configured to depart from the reliance upon an adhesive patch as the primary method of transmitter attachment to the patient so that it is not substantially affected by the patient's bodily fluids, cosmetics, lotions, body hair, skin type/condition or any other factor that may potentially weaken the adhesive condition of the adhesive patch. Moreover, in one embodiment, the base material 101 of the integrated transmitter unit and sensor insertion mechanism 100 may be formulated to provide some measure of moisture vapor transmission rate (MVTR) to allow the patient's skin to breath or ventilate.

In the manner described above, in accordance with one embodiment, there is provided an integrated sensor and transmitter device including a base unit configured for mounting onto a skin of a patient, a transmitter unit integrally provided in the base unit, a sensor assembly disposed on a surface of the base unit, the sensor assembly including a sensor configured to couple to the transmitter unit.

The base unit may be flexible, and further, may include a first end segment and a second end segment, the first end segment configured to couple to the second end segment so as to retain the base unit on the skin of the patient. Moreover, in one embodiment, the first end segment may include a Velcro hook and the second end segment may include Velcro latch.

The transmitter unit in one embodiment may include flexible electronic circuitry, where in certain embodiments the electronic circuitry may be laminated into the base unit.

Additionally, the transmitter unit may be configured to substantially conform to the shape of the base unit.

The sensor assembly in one embodiment may include an introducer coupled to at least a portion of the sensor, the introducer configured to transcutaneously position at least the portion of the sensor.

The introducer may be configured to transcutaneously position at least the portion of the sensor to be in fluid contact with a biological fluid of the patient, where the biological fluid of the patient includes interstitial fluid or blood of the patient.

Further, the introducer may be configured to be detachably removed from the sensor assembly after at least the portion of the sensor is transcutaneously positioned.

Additionally, the introducer may be configured to transcutaneously position at least the portion of the sensor at an angle other than about 90 degrees relative to the surface of the patient's skin.

In a further embodiment, the sensor assembly may be configured to substantially pivot onto the base unit so that the sensor is in signal communication with the transmitter unit.

Moreover, the sensor in one embodiment is an analyte sensor. The sensor may be configured to detect any analyte such as glucose, lactate, etc. Additional analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. A sensor may be configured to detect two or more analytes such as two or more analyte mentioned herein.

An apparatus in a further embodiment of the present invention includes a flexible base unit including an outer surface and an inner surface, said inner surface configured to contact a skin of a patient, a sensor assembly including a sensor disposed in the sensor assembly, and an introducer substantially provided in the sensor assembly to couple to at least a portion of the sensor; the introducer configured to position at least a portion of the sensor transcutaneously through the skin of the patient, and a transmitter unit integrally disposed in the base unit, the transmitter unit configured to receive one or more signals from the sensor.

The introducer may be configured to be removably detached from the sensor assembly after at least the portion of the sensor is transcutaneously positioned.

Moreover, the one or more signals from the sensor may substantially correspond to a respective one or more analyte levels of the patient.

Additionally, the transmitter unit may be configured to wirelessly (or otherwise) transmit data corresponding to the one or more signals received from the sensor, where a receiver unit may be additionally provided and configured to receive data from the transmitter unit, where the received data corresponds to one or more analyte levels of the patient. Either or both of the transmitter or receiver may be a transceiver.

The base unit in one embodiment may be configured to be securely attached substantially around one of an arm, a torso, a thigh, a calf, a waist or wrist of the patient. In certain embodiments, the base unit is flexible.

A method in accordance with still another embodiment of the present invention includes the steps of securing a transmitter unit substantially around a body part of a patient, and introducing at least a portion of a sensor through the skin of the patient so that the portion of the sensor is in fluid contact with a biological fluid of the patient, and further, where the sensor is in electrical contact with the transmitter unit.

A system in accordance with yet a further embodiment of the present invention includes an integrated housing including a transmitter unit and a sensor; the integrated housing configured for mounting onto a skin of a patient, and a sensor introducer assembly mounted onto the integrated housing, the introducer assembly configured to position at least a portion of the sensor under the skin of the patient, where the transmitter unit is in electrical contact with the sensor, and configured to transmit one or more signals corresponding a respective one or more signals received from the sensor.

In another embodiment, the system may further include a receiver unit configured to receive the one or more signals transmitted by the transmitter unit, where the receiver unit may include one of an infusion pump, a monitoring device, a personal digital assistant, a pager, or a mobile telephone.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A system, comprising:
   an integrated housing having electronics including a transmitter unit and a sensor; the integrated housing configured for mounting onto a skin of a patient; and
   a sensor introducer assembly mounted onto the integrated housing, the introducer assembly configured to position at least a portion of the sensor under the skin of the patient;
   wherein the transmitter unit is coupled to and in electrical contact with the sensor, and configured to transmit one or more signals corresponding a respective one or more signals received from the sensor;
   wherein a portion of the electronics is configured to be selectively disabled after a predetermined time period has elapsed since coupling to the sensor;
   wherein the integrated housing further comprises at least one sensor insertion location for extending the portion of the sensor therethrough; and further
   wherein the integrated housing further comprises a plurality of sensor insertion locations.

2. The system of claim 1 further including a receiver unit configured to receive the one or more signals transmitted by the transmitter unit.

3. The system of claim 2 wherein the receiver unit includes one of an infusion pump, a monitoring device, a personal digital assistant, a pager, or a mobile telephone.

4. A system, comprising:
   a housing configured for mounting onto a skin of a patient and comprising at least one sensor insertion location therethrough;
   a sensor having a portion configured to be positioned through the at least one sensor insertion location and then within the skin of a patient; and a transmitter integrally provided within the housing, wherein the transmitter is electrically coupled to the sensor by an electrical connection within the housing extending between the transmitter and the at least one sensor insertion location when the sensor is operatively positioned within the skin and wherein the electrical connection is configured to be selectively disabled after a predetermined time period has elapsed since coupling to the sensor;

wherein the housing comprises a plurality of sensor insertion locations and a plurality electrical connections, and further wherein there is a one for one correlation between the locations and the number of electrical connections.

5. The system of claim 4 further comprising a sensor introducer configured to transcutaneously position at least a portion of the sensor within the skin of the patient.

6. The system of claim 5 wherein the introducer is configured to be removed from the system after insertion of the sensor within the skin.

7. The system of claim 5 wherein the introducer is configured to be substantially housed within the system after insertion of the sensor within the skin.

8. The system of claim 4 wherein the housing is flexible to substantially conform to the shape of a body portion to which it is mounted.

9. A method, comprising:
securing a housing substantially around a body part of a patient, the housing comprising an integrated electronics including a transmitter unit and a plurality of sensor insertion apertures therethrough, wherein an electrical connection is provided between the electronics and each of the sensor insertion apertures;
inserting at least a portion of a sensor through a sensor insertion aperture and into the skin of the patient so that the portion of the sensor is in fluid contact with a biological fluid of the patient, and further wherein the sensor is in electrical contact with the transmitter unit;
transmitting data associated with the signals received from the sensor; and
disabling a portion of the electronics at the sensor insertion location through which the sensor has been inserted after a predetermined time period has elapsed since the sensor has been in electrical contact with the transmitter unit.

10. The method of claim 9 further comprising inserting a second sensor into a second sensor insertion location and into the skin of the patient, and disabling the electrical connection between the electronics and the second insertion location after the predetermined time period has elapsed.

11. The method of claim 10 further comprising inserting additional sensors individually within the other available sensor insertion locations, one at a time upon elapsing of the predetermined time period.

12. The method of claim 11 further comprising rendering the transmitter unit unusable after a predetermined number of uses.

13. The method of claim 12 wherein the predetermined number of uses corresponds to the number of sensor insertion locations.

14. The method of claim 9 wherein the predetermined time period comprises about 1 day or more.

15. The method of claim 9 wherein the inserting at least the portion of the sensor is performed manually.

16. The method of claim 9 wherein the inserting at least the portion of the sensor comprises using an automated mechanism.

17. The system of claim 1 wherein the introducer assembly is configured to be removably detached from the integrated housing after the inserting at least the portion of the sensor.

18. The system of claim 1 wherein the one or more signals from the sensor substantially corresponds to a respective one or more analyte levels of the patient.

19. The system of claim 1 wherein the transmitter unit is configured to wirelessly transmit data corresponding to the one or more signals received from the sensor.

20. The system of claim 1 wherein the sensor is an analyte sensor.

21. The system of claim 20 wherein the analyte sensor is a glucose sensor.

22. The system of claim 1 wherein the predetermined time period comprises about 1 day or more.

23. The system of claim 4 wherein the sensor is an analyte sensor.

24. The system of claim 23 wherein the analyte sensor is a glucose sensor.

25. The system of claim 4 wherein the predetermined time period comprises about 1 day or more.

* * * * *